United States Patent [19]
Yale

[11] 3,935,230
[45] Jan. 27, 1976

[54] α, α, α, α', α', α'-HEXAFLUORODI-M-TOLYLAMINE DERIVATIVES

[75] Inventor: Harry Louis Yale, New Brunswick, N.J.

[73] Assignee: E. R. Squibb & Sons, Inc., Princeton, N.J.

[22] Filed: June 14, 1974

[21] Appl. No.: 479,243

Related U.S. Application Data

[62] Division of Ser. No. 300,049, Oct. 24, 1972, Pat. No. 3,830,842, which is a division of Ser. No. 71,234, Sept. 10, 1970, Pat. No. 3,712,921.

[52] U.S. Cl............................................. 260/268 R
[51] Int. Cl.$^2$........................................ C07D 295/12
[58] Field of Search ............................... 260/268 R

[56]         References Cited
         UNITED STATES PATENTS
3,712,921   1/1973   Yale.............................. 260/268 R
3,812,177   5/1974   Engelhart et al................ 260/268 R Primary Examiner—Raymond V. Rush
Attorney, Agent, or Firm—Lawrence S. Levinson; Merle J. Smith; Donald J. Barrack

[57]            ABSTRACT

α, α, α, α', α', α'-Hexafluorodi-m-tolylamine derivatives are provided having the structure

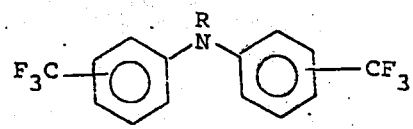

wherein R is as defined hereinafter. These compounds are useful as antibacterial agents and in the treatment of hypertension.

6 Claims, No Drawings

α, α, α, α', α', α'-HEXAFLUORODI-M-TOLYLAMINE DERIVATIVES

This application is a division of copending U.S. patent application Ser. No. 300,049, filed Oct. 24, 1972, and issued Aug. 20, 1974, as U.S. Pat. No. 3,830,842, which is a division of U.S. application Ser. No. 71,234, filed Sept. 10, 1970 and issued Jan. 23, 1973 as U.S. Pat. No. 3,712,921.

The present invention relates to α, α, α, α', α', α'-hexafluorodi-m-tolylamine derivatives having the structure

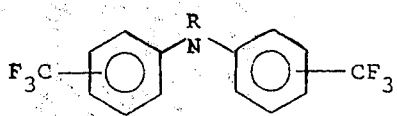

wherein R is

or lower alkylene-$NR^2R^3$, wherein $R^1$ can be hydrogen, lower alkyl, lower alkoxy, aralkyl, monocyclic cycloalkyl, and monocyclic aryl; $R^2$ and $R^3$ can be the same or different and can be hydrogen, lower alkyl, aralkyl, monocyclic cycloalkyl, hydroxy-Lower alkyl, or hydroxy lower alkoxy-lower alkyl, and $R^2$ and $R^3$ can be taken together with the nitrogen to form a 5 to 7 membered monocyclic heterocyclic ring; and to non-toxic acid-addition salts thereof.

The term "lower alkyl" as employed herein includes both straight and branched chain radicals of up to and including eight carbon atoms, for instance, methyl, ethyl, propyl, isopropyl, butyl, s-butyl, t-butyl, isobutyl, pentyl, hexyl, isohexyl, heptyl, 4,4-dimethylpentyl, octyl, 2,2,4-trimethylpentyl and the like.

The term "lower alkoxy" includes straight and branched chain lower alkyl groups attached to an oxygen.

The term "monocyclic aryl" as employed herein includes monocyclic carbocyclic aryl radicals, for instance, phenyl and substituted phenyl radicals, including lower alkylphenyl, such as tolyl, ethylphenyl, butylphenyl and the like, di(lower alkyl)phenyl, (e.g., dimethylphenyl, 3,5-diethylphenyl and the like), halophenyl (e.g., chlorophenyl, bromophenyl, and 2,4,5-trichlorophenyl) and nitrophenyl.

The term "monocyclic cycloalkyl" includes cyclic radicals containing from 3 to 6 ring members (e.g., cyclopropyl, cyclobutyl, cyclopentyl and cyclohexyl).

The term "lower alkylene" encompasses straight chain [$(CH_2)_n$ where $n$ is 2 to 8] or branched bivalent lower alkyl groups containing from 2 to 8 carbon atoms.

Examples of the basic nitrogen containing radical symbolized by the group (II)    

include amino, lower alkylamino, e.g., methylamino, ethylamino, di(lower alkyl)amino, e.g., dimethylamino, diethylamino, dipropylamino, (hydroxy-lower alkyl)amino, e.g., β-hydroxyethylamino, di(hydroxy-lower alkyl)amino, e.g., di(hydroxyethyl)amino, phenyl(lower alkyl)amino, e.g., benzylamino, and phenethylamino.

As indicated above, the nitrogen may join with the groups represented by $R^2$ and $R^3$ to form a 5 to 7 membered monocyclic heterocyclic containing, if desired, an oxygen, sulfur or an additional nitrogen atom, (not more than two hetero atoms altogether), that is, the two symbols $R^2$ and $R^3$ represent together tetramethylene, pentamethylene, hexamethylene, oxapentamethylene, oxatetramethylene, azahexamethylene, azapentamethylene, azatetramethylene, thiapentamethylene or thiatetramethylene. The heterocyclic group may also be substituted by one or two groups represented by $R^1$, $R^2$ or $R^3$.

Illustrative heterocyclic groups include piperidino, e.g., methylpiperidino, di(lower alkyl)piperidino, e.g., dimethylpiperidino, (lower alkoxy)piperidino, e.g., methoxypiperidino, pyrrolidino, (lower alkyl)pyrrolidino, e.g., 2-methylpyrrolidino, di(lower alkyl)pyrrolidino, e.g., 2,5-dimethylpyrrolidino, (lower alkoxy)pyrrolidino, e.g., ethoxypyrrolidino, morpholino, (lower alkyl)morpholino, e.g., 3-methylmorpholino or 2-methylmorpholino, di(lower alkyl)morpholino, e.g., 2,3-dimethylmorpholino, (lower alkoxy)morpholino, e.g., 2- or 3-ethoxymorpholino, thiamorpholino, (lower alkyl)thiamorpholino, e.g., 3-methylthiamorpholino or 2-methylthiamorpholino, di(lower alkyl)thiamorpholino, e.g., 2,3-diethylthiamorpholino or 2,3-dimethylthiamorpholino, (lower alkoxy)thiamorpholino, e.g., 2-methoxythiamorpholino, piperazino, (lower alkyl)piperazino, e.g., 4-methylpiperazino, 2-methylpiperazino, di(lower alkyl)piperazino, e.g., 2,3-dimethylpiperazino, hydroxy-lower alkylpiperazino, e.g., 4-(2-hydroxyethyl) piperazino, hexamethyleneimino and homopiperazino.

Preferred are those compounds wherein R is —$(CH_2)_3NR^2R^3$ and $R^2$ and $R^3$ are alkyl and/or hydrogen.

Examples of compounds falling within the present invention include, but are not limited to, the following:

1.  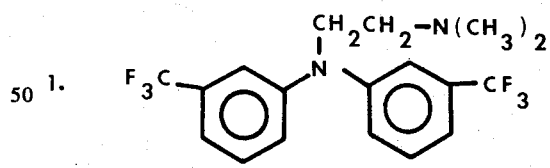

2.  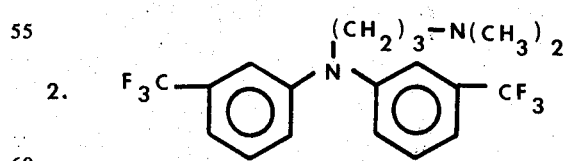

3.  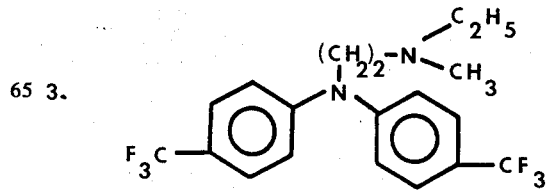

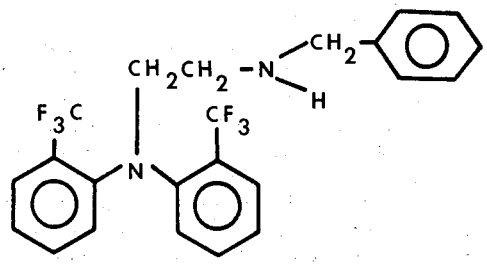
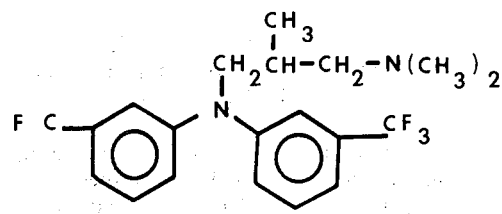

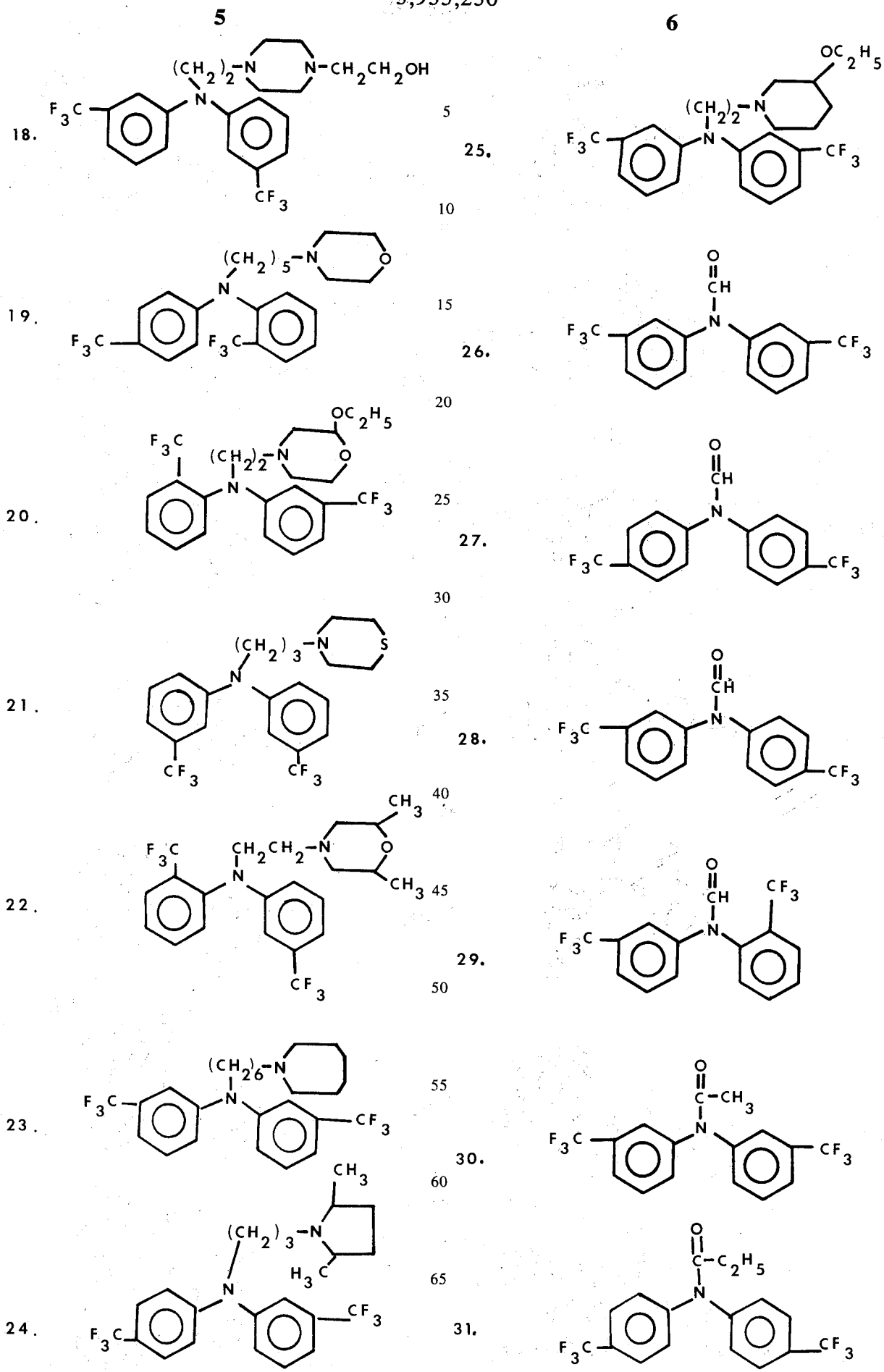

32. 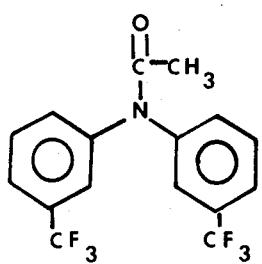
39. 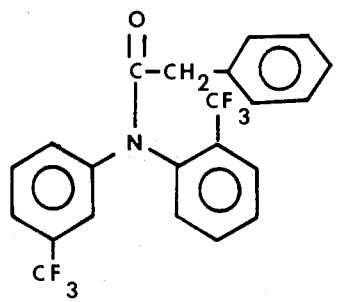
33. 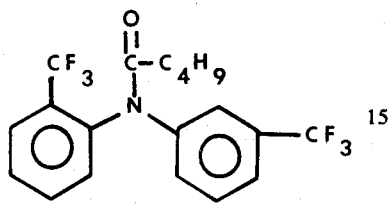
40. 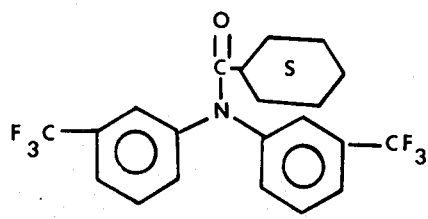
34. 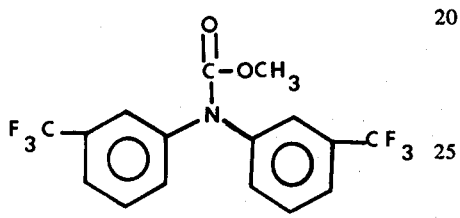
41. 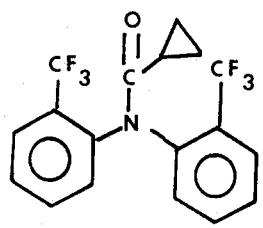
35. 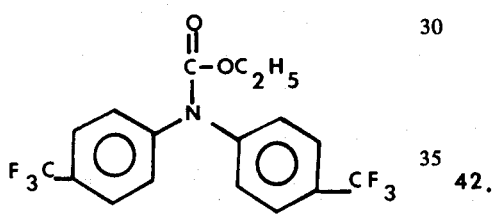
42. 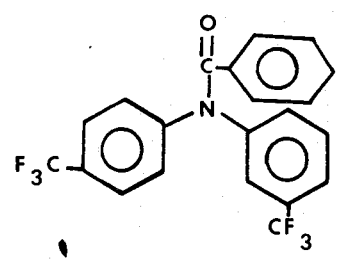
36. 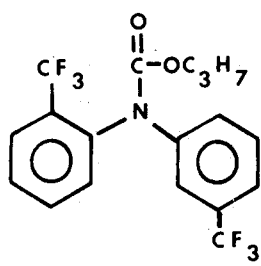
43. 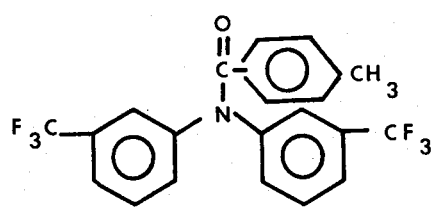
37. 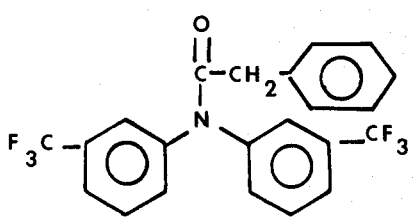
44. 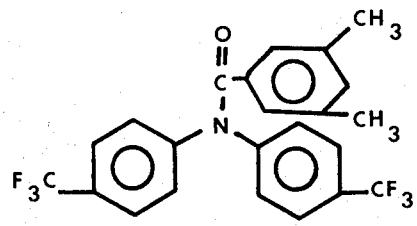
38. 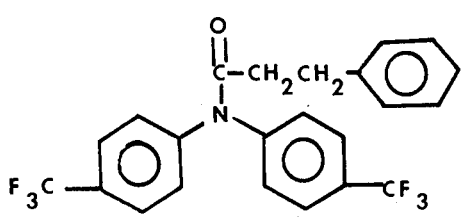
45. 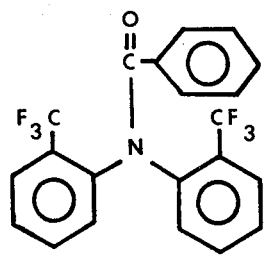

The compounds of formula I wherein R is

and R¹ is hydrogen can be prepared by reacting an α, α, α, -α′, α′, α′-hexafluoro-di-tolylamine of the structure II 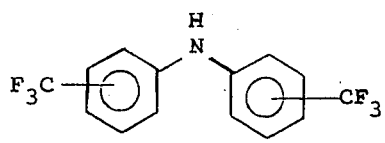

with formic acid at a temperature within the range of from about 80° to about 100°C, in an oxygen-free atmosphere. The amine is employed in a molar ratio to the acid of within the range of from about 0.1:1 to about 1:1.

The α, α, α, α′, α′, α′-hexafluoro-di-tolylamine is known in the art and can be prepared by the reaction of a halobenzotrifluoride, e.g., m-bromobenzotrifluoride or o-chlorobenzotrifluoride, with an acylamidobenzotrifluoride, e.g., m-acetamid obenzotrifluoride or p-benzamidobenzotrifluoride, in a solvent like nitrobenzene, with powdered anhydrous K₂CO₃ and a copper catalyst, at 190°–210°, followed by hydrolysis of the N-acyl group.

Compounds of formula I wherein R is

and R¹ is other than hydrogen can be prepared by acylating an aminobenzotrifluoride of the structure III 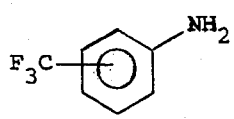

by reacting it with an acid anhydride of the structure

IV 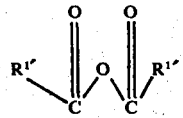

or an acyl halide of the structure

IV A 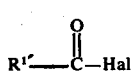

wherein R¹ is lower alkyl, lower alkoxy, aralkyl, monocyclic cycloalkyl, or monocyclic aryl, and Hal can be Cl, Br, or I, in a molar ratio of aminobenzotrifluoride: acylating agent of within the range of from about 0.1:1 to about 1:1 to form a compound of the structure V 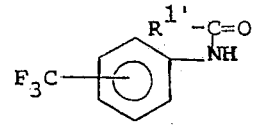

Compound V is reacted with a halobenzotrifluoride of the structure

VI 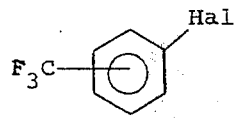

wherein Hal can be Br, Cl or I in a molar ratio of V: VI of within the range of from about 0.8:1 to about 1:1 in the presence of anhydrous alkali metal carbonate and copper catalyst and an aprotic solvent such as nitrobenzene, diethylbenzene, diethylacetamide, or dimethylformamide, in an oxygen free atmosphere, at a temperature within the range of from about 150° to about 210°C, to form a compound of the structure VII 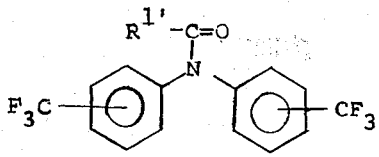

Compounds of formula I wherein R is —(CH₂-)ₙ—NR²R³ can be prepared by reacting an α, α, α, α′, α′, α′, -hexafluoro-di-tolylamine of the structure II, with a base such as a metal hydride, for example, sodium hydride, in the presence of an aprotic solvent, such as dimethylsulfoxide, dimethylformamide, xylene, diethylbenzene, or toluene, to form the anion reacting the anion of VII with a halide of the structure VIII  Hal-lower alkylene-NR²R³ wherein Hal is Cl, Br or I, in a molar ratio of II: VIII of within the range of from about 0.9:1 to about 1:1, in the presence of an alkali metal halide, such as sodium iodide, in an oxygen-free atmosphere.

Examples of halides of the structure VIII suitable for use in preparing compounds of the invention include the following: dimethylaminoethyl chloride, dimethylaminopropyl chloride, methylethylaminomethyl bromide, ethyl-isopropylaminobutyl iodide, methylamino-ethyl chloride, aminopropylbromide, methylbenzylaminopentyl chloride, cyclohexylaminoethyl bromide, hydroxyethylaminohexyl iodide, hydroxyethoxyethylaminopropyl chloride, pyrrolidinoethyl chloride, piperidinopropyl iodide, piperazinobutyl chloride, morpholinopentyl bromide, thiamorpholinohexyl iodide as well as alkylene halides containing substituted heterocyclics as indicated hereinbefore.

The bases of formula I form pharmaceutically acceptable acid-addition salts by reaction with the common inorganic and organic acids. Such inorganic salts as the hydrohalides, e.g., hydrobromide, hydrochloride, hydroiodide, sulfates, nitrates, phosphates, borates, etc., and organic salts as acetate, oxalate, tartrate, malate, citrate, succinate, benzoate, ascorbate, salicylate, theophyllinate, camphorsulfonate, alkanesulfonate, e.g., methanesulfonate, arylsulfonate, e.g., benzenesulfonate, toluenesulfonate and the like are also within the scope of the invention. It is frequently convenient to effect the purification of the product by forming the acid salt. The base may be obtained therefrom by neutralization with an alkali hydroxide such as sodium hydroxide and the base in turn can be transformed into a different salt by reaction with the appropriate acid.

The new compounds of this invention have activity upon the central nervous system and are especially active as central nervous system depressants. They may be used as tranquilizers in the alleviation of anxiety and tension states in mammals, e.g., rats, dogs or cats. They may be administered orally or parenterally in the form of tablets, capsules, elixirs, injectables or the like by incorporating the appropriate dosage of the base of formula I or a physiologically acceptable acid addition salt thereof, e.g., about 1 to 50 mg., preferably about 2.5 to 15 mg./kg/per day in two to four divided doses, in a conventional vehicle according to accepted pharmaceutical practice.

Furthermore, the new compounds of formula I are useful as antimicrobial agents and may be used to combat infections in animal species, such as mice, rats, dogs, quinea pigs and the like, due to organisms such as *Trichomonas vaginalis, Trichomonas foetus, Staphylococcus aureus, Salmonella schottmuelleri, Klebsiella pneumoniae, Proteus vulgaris, Escherichia coli, C. albicans* or *Trichophyton mentagrophytes*. For example, a compound or mixture of compounds of formula I or physiologically acceptable acid addition salt or quaternary ammonium salt thereof may be administered orally to an infected animal, e.g., to a mouse, in an amount of about 5 to 25 mg. per kg. per day in 2 to 4 divided doses. These may be conventionally formulated in a tablet, capsule or elixir containing about 10 to 250 mg. per dosage unit, by compounding the active substance or substances with the conventional excipient, vehicle, binder, preservative, flavor, etc., as called for by accepted pharmaceutical practice. They may also be applied topically, e.g., to dermatophytosis in a guinea pig, in a lotion, salve or cream at a concentration of about 0.01 to 3 percent by weight.

They may also be used as surface disinfectants. About 0.01 to 1 percent by weight of any of these substances may be dispersed on an inert solid or in a liquid such as water and applied as a dust or spray. They may be incorporated also, for example, in a soap or other cleansing agent, e.g., a solid or liquid detergent, detergent composition, for example, in general cleaning, in cleaning dairy barns or equipment or cleaning food handling or processing equipment.

The following examples are illustrative of the invention. All temperatures are on the Centigrade scale.

EXAMPLE 1

N,N-Bis-($\alpha,\alpha,\alpha$-trifluoro-m-tolyl)formamide

A solution of 8 g. of $\alpha, \alpha, \alpha, \alpha', \alpha', \alpha'$-hexafluorodi-m-tolylamine in 70 ml. of 98-100% formic acid is heated at 95°–100° with stirring, in an atmosphere of nitrogen, for 4 hours. The excess formic acid is removed in vacuo, and the residue is recrystallized from pentane to give 6.8 g. of N,N,bis-($\alpha, \alpha, \alpha$-trifluoro-m-tolyl)formamide, m.p. about 63°–65°.

EXAMPLES 2 to 5

Using the procedure of Example 1, but replacing the $\alpha, \alpha, \alpha, \alpha', \alpha', \alpha'$-hexafluoro-di-m-tolylamine by
A. N,N-bis($\alpha, \alpha, \alpha$-trifluoro-o-tolyl)amine
B. N-($\alpha, \alpha, \alpha$-trifluoro-m-tolyl)-N-($\alpha', \alpha', \alpha'$-trifluoro-o-tolyl)amine
C. N,N-bis($\alpha, \alpha, \alpha$-trifluoro-p-tolyl)amine
D. N-($\alpha, \alpha, \alpha$-trifluoro-p-tolyl)-N-($\alpha', \alpha', \alpha'$-trifluoro-m-tolyl)amine
there is obtained, respectively Example 2 — N,N-bis-($\alpha, \alpha, \alpha$-trifluoro-o-tolyl)formamide Example 3 — N-($\alpha, \alpha, \alpha$-trifluoro-m-tolyl)-N-($\alpha', \alpha', \alpha'$-trifluoro-o-tolyl)formamide Example 4 — N,N-bis($\alpha, \alpha, \alpha$-trifluoro-p-tolyl)formamide Example 5 — N-($\alpha, \alpha, \alpha$-trifluoro-p-tolyl)N-($\alpha', \alpha', \alpha'$-trifluoro-m-tolyl)formamide

EXAMPLE 6

A. Aceto-m-$\alpha, \alpha, \alpha$-trifluorotoluidine

A solution of 193.2 g. of m-aminobenzotrifluoride in 3 liters of water and 100 ml. of concd. hydrochloric acid is stirred with 140 ml. of acetic anhydride at room temperature. The reaction becomes exothermic and a granular solid separates from solution. After stirring for 20 minutes the reaction mixture is cooled, and the solid recovered by filtration to give 150.8 g., of aceto-m-$\alpha, \alpha, \alpha$-trifluorotoluidine m.p. about 103°–105°.

B. N,N-bis($\alpha, \alpha, \alpha$-trifluoro-m-tolyl)acetamide

A suspension of 152 g. of anhydrous potassium carbonate, 3.5 g. of copper bronze, 225 g. of aceto-m-$\alpha, \alpha, \alpha$-trifluorotoluidine, and 305 g. of m-bromobenzotrifluoride in 2 liters of nitrobenzene is heated under reflux, with stirring, in an atmosphere of nitrogen for 22 hours. After cooling, the reaction mixture is filtered, and the filtrate is concentrated in vacuo, to give 273 g. of N,N-bis($\alpha, \alpha, \alpha$-trifluoro-m-tolyl)acetamide, m.p. about 73°–74°.

EXAMPLES 7 to 18

Using the procedure of Example 6 but substituting the $\alpha, \alpha, \alpha$-trifluorotoluidine shown in column 1 of Table I below and the acylating agent shown in column 2, and the halo-$\alpha, \alpha, \alpha$-trifluorotoluene shown in column 3, the product shown in column 4 is obtained.

Table I

| Ex. No. | Column 1<br>α,α,α-Trifluorotoluidine | Column 2<br>Acid anhydride | Column 3<br>Halo-α,α,α-tri-fluorotoluene | Column 4<br>Product |
|---|---|---|---|---|
| 7 | 2-CF$_3$ aniline | (C$_2$H$_5$CO)$_2$O | 2-Cl, 1-CF$_3$ benzene | N-(2-CF$_3$-phenyl)-N-(2-CF$_3$-phenyl)propanamide |
| 8 | 4-CF$_3$ aniline | (C$_3$H$_7$CO)$_2$O | 4-Br, 1-CF$_3$ benzene | N,N-bis(4-CF$_3$-phenyl)butanamide |
| 9 | 3-CF$_3$ aniline | (CH$_3$CO)$_2$O | 4-Cl, 1-CF$_3$ benzene | N-(3-CF$_3$-phenyl)-N-(4-CF$_3$-phenyl)acetamide |
| 10 | 3-CF$_3$ aniline | (C$_5$H$_{11}$CO)$_2$O | 3-Br, 1-CF$_3$ benzene | N,N-bis(3-CF$_3$-phenyl)hexanamide |
| 11 | 4-CF$_3$ aniline | (C$_7$H$_{15}$CO)$_2$O | 3-Cl, 1-CF$_3$ benzene | N-(4-CF$_3$-phenyl)-N-(3-CF$_3$-phenyl)octanamide |
| 12 | 2-CF$_3$ aniline | (PhCH$_2$CO)$_2$O | 3-I, 1-CF$_3$ benzene | N-(2-CF$_3$-phenyl)-N-(3-CF$_3$-phenyl)phenylacetamide |
| 13 | 3-CF$_3$ aniline | (PhC$_2$H$_4$CO)$_2$O | 3-Cl, 1-CF$_3$ benzene | N,N-bis(3-CF$_3$-phenyl)-3-phenylpropanamide |
| 14 | 4-CF$_3$ aniline | (thienyl-CO)$_2$O | 4-I, 1-CF$_3$ benzene | N,N-bis(4-CF$_3$-phenyl)thiophenecarboxamide |
| 15 | 3-CF$_3$ aniline | (PhCO)$_2$O | 3-Cl, 1-CF$_3$ benzene | N,N-bis(3-CF$_3$-phenyl)benzamide |
| 16 | 4-CF$_3$ aniline | (PhCO)$_2$O | 4-Br, 1-CF$_3$ benzene | N,N-bis(4-CF$_3$-phenyl)benzamide |
| 17 | 2-CF$_3$ aniline | (4-CH$_3$-C$_6$H$_4$CO)$_2$O | 3-Cl, 1-CF$_3$ benzene | N-(2-CF$_3$-phenyl)-N-(3-CF$_3$-phenyl)-4-methylbenzamide |
| 18 | 2-CF$_3$ aniline | (3,5-diethyl-CH$_3$-benzoyl)$_2$O | 4-Br, 1-CF$_3$ benzene | N-(2-CF$_3$-phenyl)-N-(3-CF$_3$-phenyl)-3-methyl-5-ethylbenzamide |

EXAMPLE 19

A. α,α,α, α', α', α'-Hexafluorodi-m-tolylamine

A solution of 271 g. of N,N-bis(α, α, α-trifluoro-m-tolyl)acetamide in 3 liters of 95% ethanol and 800 ml. of concentrated hydrochloric acid is heated under reflux with stirring for 3 hours. The reaction mixture is concentrated in vacuo, the residue is taken up in 600 ml. of ether, washed with 500 ml. of water, then with 100 ml. of 2% sodium hydroxide, and then with water. After drying the solvent is removed by distillation and the residue is fractionated in vacuo to yield 143 g. of α, α, α, α', α',α'-hexafluorodim-tolylamine, b.p. about 94°–98°/0.2 mm., $n_D^{26}$ 1.5140.

B. N,N-Dimethyl-N', N'-bis(α, α, α-trifluoro-m-tolyl)-1,3-propanediamine

A solution of 9 g. of α, α, α, α', α', α'-hexafluorodim-tolylamine in 60 ml. of dimethyl sulfoxide is stirred at room temperature under nitrogen and 2.5 g. (0.05 mole) of sodium hydride (50% in mineral oil) is added in small increments over a period of 45 minutes. The reaction temperature increases spontaneously to 38°. Following the addition the reaction temperature is gradually increased to 50°. After 15 minutes at 50° the reaction mixture is cooled to 30° and 30 ml. of 2N dimethylaminopropyl chloride in toluene is added followed by 0.5 g. of sodium iodide. The reaction mixture is heated at 65°–75° for 4 hours. After cooling to room temperature 7 ml. of ethanol is added. The reaction mixture is poured with stirring into 700 ml. of ice-water. The oil which separates from solution is extracted into 400 ml. of ether. The ethereal solution is washed with water and extracted with 100 ml. of 2.5% hydrochloric acid. The ethereal mother liquor is taken to dryness and triturated with diisopropyl ether to give 10 g. of solid, m.p. 63–65°, recrystallization from 200 ml. of diethyl ether gives 6.6 g. of product, m.p. about 65°–66° (dec.).

EXAMPLE 20

N,N-Dimethyl-N', N'-bis(α,α, α-trifluoro-m-tolyl)-ethylene diamine, hydrochloride A solution of 18 g. of α, α, α, α', α', α'-hexafluorodim-tolylamine in 120 ml. of dimethyl sulfoxide is stirred at room temperature under nitrogen and 5 g. of sodium hydride (50% in mineral oil) in added in small increments over a period of 45 minutes. The reaction temperature increases spontaneously to 38°. Following the addition the reaction temperature is gradually increased to 50°. After 15 minutes at 50° the reaction mixture is cooled to 30° and 10 g. of dimethylaminoethyl chloride is added. The reaction mixture is heated 85°–90° for 2 hours. After cooling to room temperature 5 ml. of 95% ethanol is added. The reaction mixture is poured with stirring into 1200 ml. of cold water. The oil which separates from solution is extracted into ether, the solution is washed with water, dried, and the solvent removed. The residue, 19 g., is taken up into 300 ml. of ether. The ethereal solution is extracted with 200 ml. of 2% hydrochloric acid, the ether is dried, filtered, and taken to dryness. The residue of 20.6 g. crystallizes. After trituration with 200 ml. of diisopropyl ether the solid is filtered to give 9 g. of solid, m.p. 120°–125° (dec.). It is recrystallized from acetonitrile-ether to give 6.3 g. of product, m.p. about 131°–133° (dec.).

EXAMPLES 21 to 45

Using the procedure of Example 19, but substituting the α, α, α, α', α', α'-hexafluorodi-tolylamine shown in column 1 of Table II below and the aminoalkylene halide shown in column 2 of Table II, the product shown in column 3 is obtained.

Table II

| Ex. No. | Column 1<br>α,α,α,α',α',α'-Hexa-flouro-tolylamine | Column 2<br>Hal-lower alkylene-NR$^2$R$^3$ | Column 3<br>Product |
|---|---|---|---|
| 21 | F$_3$C-C$_6$H$_4$-NH-C$_6$H$_4$-CF$_3$ (3,3') | Cl-(CH$_2$)$_4$-N(C$_5$H$_{11}$)(CH$_3$) | F$_3$C-C$_6$H$_4$-N((CH$_2$)$_4$-N(C$_5$H$_{11}$)(CH$_3$))-C$_6$H$_4$-CF$_3$ |
| 22 | F$_3$C-C$_6$H$_4$-NH-C$_6$H$_4$-CF$_3$ (3,2') | Br-(CH$_2$)$_3$-NH-C$_4$H$_9$ | F$_3$C-C$_6$H$_4$-N((CH$_2$)$_3$-NH-C$_4$H$_9$)-C$_6$H$_4$-CF$_3$ |
| 23 | F$_3$C-C$_6$H$_4$-NH-C$_6$H$_4$-CF$_3$ (4,4') | I-(CH$_2$)$_2$-NH$_2$ | F$_3$C-C$_6$H$_4$-N((CH$_2$)$_2$NH$_2$)-C$_6$H$_4$-CF$_3$ |
| 24 | (2-CF$_3$)C$_6$H$_4$-NH-C$_6$H$_4$(2-CF$_3$) | Cl-CH$_2$-CH(CH$_3$)-CH$_2$-NH$_2$ | (2-CF$_3$)C$_6$H$_4$-N(CH$_2$-CH(CH$_3$)-CH$_2$NH$_2$)-C$_6$H$_4$(2-CF$_3$) |

3,935,230

Table II Contd.

| Ex. No. | Column 1 α,α,α,α',α',α'-Hexa-fluoro-tolylamine | Column 2 Hal-lower alkylene-NR²R³ | Column 3 Product |
|---|---|---|---|
| 25 | 4-CF₃-C₆H₄-NH-C₆H₄-3-CF₃ | Br-(CH₂)₆-NH-CH₂-C₆H₅ | (3-CF₃-C₆H₄)(4-CF₃-C₆H₄)N-(CH₂)₆-NH-CH₂-C₆H₅ |
| 26 | 4-CF₃-C₆H₄-NH-C₆H₄-3-CF₃ | Cl-(CH₂)₅-N(C₂H₄-C₆H₅)(C₂H₅) | (3-CF₃-C₆H₄)(4-CF₃-C₆H₄)N-(CH₂)₅-N(C₂H₄-C₆H₅)(C₂H₅) |
| 27 | (2-CF₃-C₆H₄)₂NH | Cl-(CH₂)₂-NH-(cyclopentyl-S) | (2-CF₃-C₆H₄)₂N-(CH₂)₂-NH-(cyclopentyl-S) |
| 28 | 2-CF₃-C₆H₄-NH-C₆H₄-4-CF₃ | Br-(CH₂)₃-N(CH₃)(cyclopropyl) | (2-CF₃-C₆H₄)(4-CF₃-C₆H₄)N-(CH₂)₃-N(CH₃)(cyclopropyl) |
| 29 | (4-CF₃-C₆H₄)₂NH | I-(CH₂)₄-NH-(CH₂)₂OH | (4-CF₃-C₆H₄)₂N-(CH₂)₄-NH-(CH₂)₂OH |
| 30 | 3-CF₃-C₆H₄-NH-C₆H₄-4-CF₃ | Cl-CH₂-CH(CH₃)-N(CH₃)-(CH₂)₃-OH | (3-CF₃-C₆H₄)(4-CF₃-C₆H₄)N-CH₂CH(CH₃)-N(CH₃)-(CH₂)₃OH |
| 31 | (2-CF₃-C₆H₄)₂NH | Br-(CH₂)₂-NH-CH₂-OCH₂-OH | (2-CF₃-C₆H₄)₂N-(CH₂)₂-NH-CH₂OCH₂OH |
| 32 | (3-CF₃-C₆H₄)₂NH | Cl-(CH₂)₅-N(CH₂CH₂OH)(CH₂-cyclohexyl-S) | (3-CF₃-C₆H₄)₂N-(CH₂)₅-N(CH₂CH₂OH)(CH₂-cyclohexyl-S) |
| 33 | (3-CF₃-C₆H₄)₂NH | Cl-(CH₂)₂-N(pyrrolidinyl) | (3-CF₃-C₆H₄)₂N-(CH₂)₂-N(pyrrolidinyl) |
| 34 | (4-CF₃-C₆H₄)₂NH | Br-(CH₂)₃-N(pyrrolidinyl) | (4-CF₃-C₆H₄)₂N-(CH₂)₃-N(pyrrolidinyl) |
| 35 | (2-CF₃-C₆H₄)₂NH | I-(CH₂)₂-N(2-methylpyrrolidinyl) | (2-CF₃-C₆H₄)₂N-(CH₂)₂-N(2-methylpyrrolidinyl) |
| 36 | 3-CF₃-C₆H₄-NH-C₆H₄-4-CF₃ | Cl-(CH₂)₂-N(piperidinyl) | (3-CF₃-C₆H₄)(4-CF₃-C₆H₄)N-(CH₂)₂-N(piperidinyl) |

Table II Contd.

| Ex. No. | Column 1 α,α,α,α',α',α'-Hexaflouro-tolylamine | Column 2 Hal-lower alkylene-NR²R³ | Column 3 Product |
|---|---|---|---|
| 37 | 2,2'-bis(CF₃) diphenylamine | Br-(CH₂)₂-N(piperazine)NH | N-[(CH₂)₂-piperazine-NH] 2,2'-bis(CF₃) diphenylamine |
| 38 | 3,3'-bis(CF₃) diphenylamine | Cl-(CH₂)₄-N(3,5-dimethylpiperidine) | N-[(CH₂)₄-3,5-dimethylpiperidine] 3,3'-bis(CF₃) diphenylamine |
| 39 | 3,4'-bis(CF₃) diphenylamine | Br-(CH₂)₂-N(piperazine)N-CH₃ | N-[(CH₂)₂-N-methylpiperazine] 3,4'-bis(CF₃) diphenylamine |
| 40 | 3,4'-bis(CF₃) diphenylamine | Cl-(CH₂)₃-N(piperazine)N-CH₂CH₂OH | N-[(CH₂)₃-N-hydroxyethylpiperazine] 3,4'-bis(CF₃) diphenylamine |
| 41 | 2,2'-bis(CF₃) diphenylamine | Cl-(CH₂)₂-N(morpholine) | N-[(CH₂)₂-morpholine] 2,2'-bis(CF₃) diphenylamine |
| 42 | 2,4'-bis(CF₃) diphenylamine | Br-(CH₂)₄-N(thiomorpholine) | N-[(CH₂)₄-thiomorpholine] 2,4'-bis(CF₃) diphenylamine |
| 43 | 4,4'-bis(CF₃) diphenylamine | Cl-(CH₂)₃-N(piperidine) | N-[(CH₂)₃-piperidine] 4,4'-bis(CF₃) diphenylamine |
| 44 | 3,3'-bis(CF₃) diphenylamine | Br-CH(CH₃)-CH₂-N(2-ethylmorpholine) | N-[CH(CH₃)CH₂-2-ethylmorpholine] 3,3'-bis(CF₃) diphenylamine |
| 45 | 2,4'-bis(CF₃) diphenylamine | Cl-(CH₂)₄-N(3,5-dimethylthiomorpholine) | N-[(CH₂)₄-3,5-dimethylthiomorpholine] 2,4'-bis(CF₃) diphenylamine |

EXAMPLE 46

Methyl-N,N-bis-(α,α,α-trifluoro-m-tolyl)carbamate

To a solution of 161 g. of m-aminobenzotrifluoride and 101 g. of triethylamine in 1.0 l. of dry benzene is added dropwise, with ice water cooling, 94.5 g. of methyl chlorocarbonate. Subsequent to the addition, the mixture is stirred and heated under reflux for 1 hour, cooled, and filtered from the precipitated triethylamine hydrochloride. The filtrate is concentrated in vacuo to give methyl m-(α, α, α-trifluorotolyl)carbamate.

The methyl m-(α, α, α-trifluorotolyl)carbamate is then reacted with a m-bromobenzotrifluoride in accordance with the procedure of Example 6 to give methyl N,N-bis (α, α, α-trifluoro-m-tolyl)carbamate.

EXAMPLE 47 n-Propyl-N,N-bis-(α,α,α-trifluoro-o-tolyl)carbamate

By substituting 161 g. of o-aminobenzotrifluoride for the m-aminobenzotrifluoride and 122.5 g. of N-propyl chlorocarbonate for the methyl chlorocarbonate in Example 47, there is obtained n-propyl o-(α, α, α-trifluorotolyl)carbamate which is reacted with a halobenzotrifluoride in accordance with Example 6 to give the above titled compound.

What is claimed is:

1. A compound of the structure

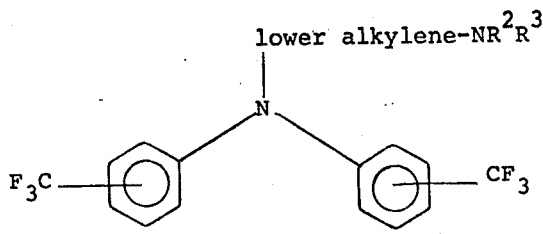

wherein $-NR^2R^3$ is piperazino, (lower alkyl)piperazino, di(lower alkyl)piperazino or 2-hydroxyethylpiperazino, or a pharmaceutically acceptable salt thereof.

2. A compound in accordance with claim 1 having the structure

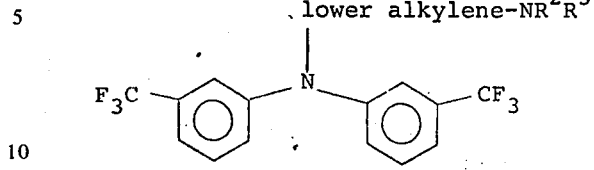

3. A compound in accordance with claim 1 wherein $-NR^2R^3$ is piperazino.

4. A compound in accordance with claim 1 wherein $-NR^2R^3$ is (lower alkyl)piperazino.

5. A compound in accordance with claim 1 wherein $-NR^2R^3$ is di(lower alkyl)piperazino.

6. A compound in accordance with claim 1 wherein $-NR^2R^3$ is 2-hydroxyethylpiperazino.

* * * * *

UNITED STATES PATENT AND TRADEMARK OFFICE
CERTIFICATE OF CORRECTION

PATENT NO. : 3,935,230
DATED : Jan. 27, 1976
INVENTOR(S) : Harry L. Yale

It is certified that error appears in the above-identified patent and that said Letters Patent are hereby corrected as shown below:

Column 4, example 11., should read:

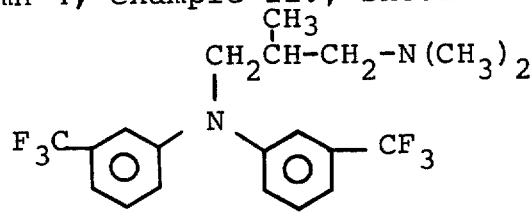

Column 10, line 1, "$R^1$" should read -- $R^{1'}$ --.

Column 13, table I, example 18 should read:

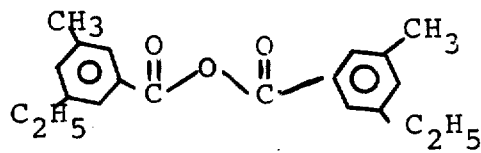

Example 32, column 2, should read:

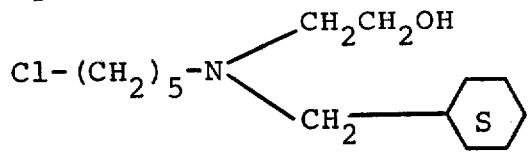

UNITED STATES PATENT AND TRADEMARK OFFICE
CERTIFICATE OF CORRECTION

PATENT NO. : 3,935,230
DATED : Jan. 27, 1976
INVENTOR(S) : Harry L. Yale

It is certified that error appears in the above-identified patent and that said Letters Patent are hereby corrected as shown below:

Column 18, example 30, column 3 should read:

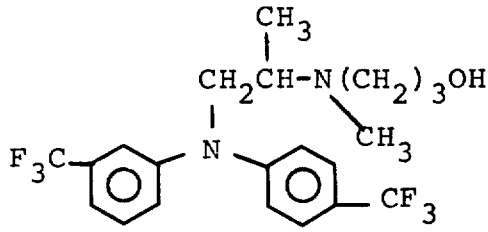

Column 18, example 36, column 3 should read:

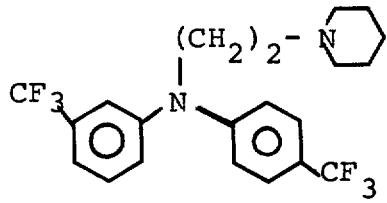

*Signed and Sealed this*

Twentieth Day of July 1976

[SEAL]

*Attest:*

RUTH C. MASON
*Attesting Officer*

C. MARSHALL DANN
*Commissioner of Patents and Trademarks*